United States Patent
Okawa

Patent Number: 5,856,545
Date of Patent: Jan. 5, 1999

[54] METHOD FOR PREPARATION OF ORGANOPENTASILOXANE

[75] Inventor: Tadashi Okawa, Chiba Prefecture, Japan

[73] Assignee: Dow Corning Toray Silicone Co., Ltd., Tokyo, Japan

[21] Appl. No.: 985,540

[22] Filed: Dec. 5, 1997

[30] Foreign Application Priority Data

Jun. 12, 1996 [JP] Japan ................... 8-342703

[51] Int. Cl.$^6$ .................................. C07F 7/08
[52] U.S. Cl. ............................ 556/440; 556/442
[58] Field of Search ........................ 556/440, 442

[56] References Cited

U.S. PATENT DOCUMENTS

| | | | |
|---|---|---|---|
| 5,262,555 | 11/1993 | Okawa et al. | 556/440 |
| 5,550,270 | 8/1996 | Takarada et al. | 556/440 |

FOREIGN PATENT DOCUMENTS

Hei 5-86075   6/1993   Japan .

Primary Examiner—Paul F. Shaver
Attorney, Agent, or Firm—Larry A. Milco

[57] ABSTRACT

A process for the production of organopentasiloxane represented by the general formula:

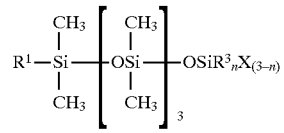

wherein $R^1$ is an acryloyloxy-containing monovalent organic group or a methacryloyloxy-containing monovalent organic group; $R^3$ is a monovalent hydrocarbon group; X is a hydrolytic group; and the subscript n is 0, 1, or 2; which is characterized subjecting (A) 1-hydroxy-organotetrasiloxane, or an organosiloxane oligomer mixture comprising it as the main component, which is obtained by hydrolyzing 1-acyloxy-organotetrasiloxane or an oganosiloxane oligomer mixture comprising it as the main component; and (B) hydrolytic silane represented by the general formula $R^3{}_n SiX_{(4-n)}$ to a condensation reaction.

30 Claims, No Drawings

METHOD FOR PREPARATION OF ORGANOPENTASILOXANE

FIELD OF THE INVENTION

The present invention relates to a process for the production of organopentasiloxane, and, more specifically, it relates to a process for efficiently producing organopentasiloxane having an acryloyloxy-containing monovalent organic group or a methacryloyloxy-containing monovalent organic group bonded to a silicon atom at one end of the molecular chain and a hydrolytic group bonded to a silicon atom at the other end of the molecular chain.

BACKGROUND OF THE INVENTION

In the past, 3-acryloyloxypropyl trimethoxysilane, 3-acryloyloxypropylmethyl dimethoxysilane, 3-methacryloyloxypropyl trimethoxysilane, 3-metacryloyloxypropylmethyl dimethoxysilane, and other organosilicon compounds with monovalent organic groups containing acryloyloxy groups or monovalent organic groups containing methacryloyloxy groups and hydrolytic groups bonded to silicon atoms have been used as silane coupling agents and raw materials for the production of crosslinkable polyolefinic resins.

However, due to the fact that the monovalent organic groups containing acryloyloxy groups or monovalent organic groups containing methacryloyloxy groups and hydrolytic groups were bonded to the same silicon atoms, the problem with these organosilicon compounds was that when they were used as silane coupling agents for the surface treatment of inorganic fillers, these functional groups ended up concealed in the crosslinked coating formed via the condensation reaction and hydrolysis, so that the effectiveness of the surface treatment was lower than expected. For this reason, when inorganic fillers obtained by surface treatment using these organosilicon compounds were compounded with silicone rubber compositions, sufficient fatigue durability could not be imparted to the silicone rubbers obtained by curing them. Also, when these organosilicon compounds were copolymerized with various olefins as raw materials for the production of crosslinked polyolefinic resins, these functional groups ended up concealed in the polyolefinic resin, and, as a result, the crosslinkability of the polyolefinic resin was lower than expected.

In the past, the authors of the present invention offered organopentasiloxanes with acryloyloxy-containing monovalent organic groups or methacryloyloxy-containing monovalent organic groups and hydrolytic groups bonded to silicon atoms and a process for their production (see Japanese Unexamined (Kokai) Patent Publication No. Hei 05(1993) -86075). The process for the production of the organopentasiloxane offered in Japanese Unexamined (Kokai) Patent Publication No. Hei 05(1993)-86075 was characterized by subjecting organopentasiloxane having a hydrogen atom bonded to a silicon atom at one end of the molecular chain and a hydrolytic group bonded to a silicon atom at the other end of the molecular chain and an alkene or alkylenoxyalkene containing methacryloyloxy groups to a hydrosilylation reaction.

However, the problem with the process for the production of the organopentasiloxane offered in Japanese Unexamined (Kokai) Patent Publication No. Hei 05(1993)-86075 was that when it was used to produce organopentasiloxanes, various side reactions were generated. When, for example, 1,1,1 -trimethoxy-3,3,5,5,7,7,9,9-octamethylpentasiloxane and allyl methacrylate were subjected to a hydrosilylation reaction, a propene-releasing b-elimination reaction described below would take place, producing the target organopentasiloxane with a 3-methacryloyloxypropyl group bonded to a silicon atom at the end of the molecular chain along with organopentasiloxane with a methacryloyloxy group bonded to a silicon atom at the end of the molecular chain and organopentasiloxane with a propyl group bonded to a silicon atom at the end of the molecular chain as by-products, which decreased the yield and purity of the target product.

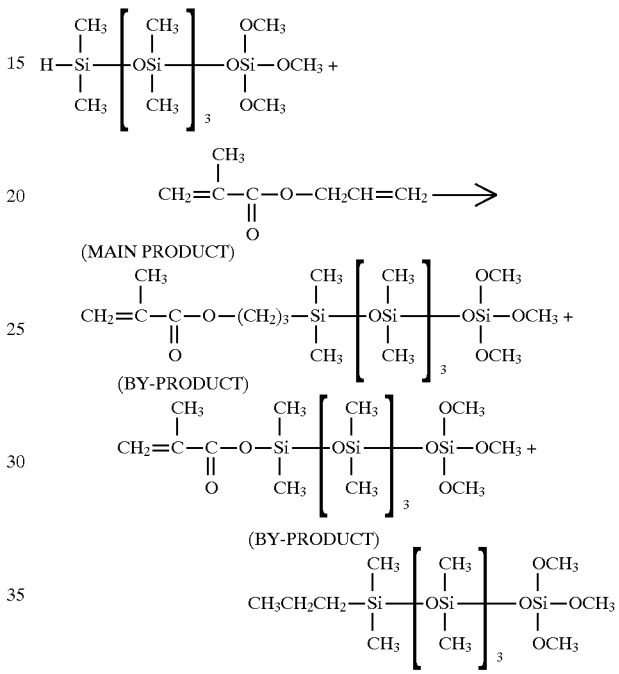

SUMMARY OF THE INVENTION

It is an object of the present invention to offer a process for efficiently producing organopentasiloxane having an acryloyloxy-containing monovalent organic group or a methacryloyloxy-containing monovalent organic group bonded to a silicon atom at one end of the molecular chain and a hydrolytic group bonded to a silicon atom at the other end of the molecular chain.

More specifically, the present invention relates to a process for the production of organopentasiloxane represented by the general formula (IV):

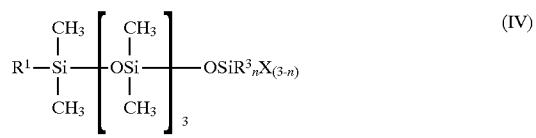

wherein $R^1, R^3, X$ and the subscript n are as defined below, which is characterized by subjecting (A) a 1-hydroxy-organotetrasiloxane, or an organosiloxane oligomer mixture comprising it as the main component, represented by general formula (II):

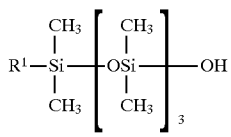

$$\begin{array}{c} CH_3 \\ | \\ R^1-Si- \\ | \\ CH_3 \end{array} \left[ \begin{array}{c} CH_3 \\ | \\ OSi- \\ | \\ CH_3 \end{array} \right]_3 OH \qquad (II)$$

wherein $R^1$ is as defined below, which is obtained by hydrolyzing 1-acyloxy-organotetrasiloxane, or an organosiloxane oligomer mixture comprising it as the main component, represented by the general formula (I):

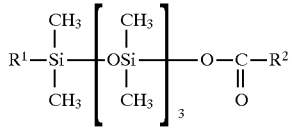

$$\begin{array}{c} CH_3 \\ | \\ R^1-Si- \\ | \\ CH_3 \end{array} \left[ \begin{array}{c} CH_3 \\ | \\ OSi- \\ | \\ CH_3 \end{array} \right]_3 O-C-R^2 \\ \phantom{aaaaaaaaaaa} \| \\ \phantom{aaaaaaaaaaa} O \qquad (I)$$

wherein $R_1$ is an acryloyloxy-containing monovalent organic group or a methacryloyloxy-containing monovalent organic group, and $R^2$ is a monovalent hydrocarbon group, and (B) a hydrolytic silane represented by the general formula (III):

$$R^3{}_n SiX_{(4-n)} \qquad (III)$$

wherein $R^3$ is a monovalent hydrocarbon group, X is a hydrolytic group, and the subscript n is 0, 1, or 2, to a condensation reaction.

DETAILED DESCRIPTION OF THE INVENTION

Below, the production process of the present invention is explained in detail.

In the production process of the present invention, first of all, 1-hydroxy-organotetrasiloxane represented by the general formula (II), or an organosiloxane oligomer mixture comprising it as the main component, is prepared by hydrolyzing 1-acyloxy-organotetrasiloxane represented by the general formula (I) or an organosiloxane oligomer mixture comprising it as the main component. The organosiloxane oligomer mixture comprising 1-acyloxy-organotetrasiloxane represented by the general formula (I) as the main component means a mixture of organosiloxane oligomers, in which an acyloxy group is bonded to a silicon atoms at the end of the molecular chain as represented by the general formula (I), but the number of siloxane units varies, and, preferably, it is a mixture containing not less than 50% of 1-acyloxy-organotetrasiloxane represented by the general formula (I). Also, in the same manner as above, the organosiloxane oligomer mixture comprising the 1-hydroxy-organotetrasiloxane represented by the general formula (II) means a mixture of organosiloxane oligomers, in which a hydroxyl group is bonded to a silicon atom at the end of the molecular chain as represented by the general formula (II), but the number of siloxane units varies, and, preferably, it is a mixture containing not less than 30% of 1-hydroxy-organotetrasiloxane represented by the general formula (II). $R^1$ in the general formula (I) is an acryloyloxy-containing monovalent organic group or a methacryloyloxy-containing monovalent organic group specifically exemplified by 3-acryloyloxypropyl, 6-acryloyloxyhexyl, and other acryloyloxyalkyl groups; 3-(2-acryloyloxyethyloxy)-propyl and other acryloyloxyalkyloxyalkyl groups; 3-methacryloyloxypropyl, 6-methacryloyloxyhexyl, and other methacryloyloxyalkyl groups; 3-(2-methacryloyloxyethyloxy)-propyl and other methacryloyloxyalkyloxyalkyl groups. Preferably, it is an acryloyloxyalkyl or methacryloyloxyalkyl group, with 3-methacryloyloxypropyl being especially preferable from the standpoint of ease of manufacture and economic efficiency. Also, $R^2$ in the general formula (I) is a monovalent group, specifically exemplified by methyl, ethyl, propyl, butyl, pentyl, and other alkyl groups; vinyl, allyl, butenyl, pentenyl, and other alkenyl groups; phenyl, tolyl, xylyl, and other allyl groups; benzyl, phenetyl, and other aralkyl groups, with methyl being especially preferable.

A method, in which hexamethylcyclotrisiloxane is subjected to a ring-opening reaction with acyloxysilane represented by the general formula (V):

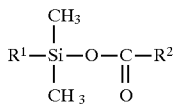

$$\begin{array}{c} CH_3 \\ | \\ R^1-Si-O-C-R^2 \\ | \qquad \| \\ CH_3 \qquad O \end{array} \qquad (V)$$

in the presence of an acidic catalyst, is suggested as the process for preparing 1-acyloxy-organotetrasiloxane represented by the general formula (I). $R^1$ in the general formula (V) is an acryloyloxy-containing monovalent organic group or a methacryloyloxy-containing monovalent organic group exemplified by the same organic groups as above. Also, $R^2$ in the general formula (V) is a monovalent hydrocarbon group exemplified by the same monovalent hydrocarbon groups as above. The acidic catalyst is exemplified by proton acid catalysts and Lewis acid catalysts, with proton acid catalysts specifically exemplified by hydrochloric acid, nitric acid, sulfuric acid, trifluoromethanesulfonic acid, trifluoracetic acid, among which trifluoromethanesulfonic acid is especially preferable, and with Lewis acid catalysts specifically exemplified by $ZnCl_2$, $BeCl_2$, $TeCl_4$, $SnCl_4$, $FeCl_3$, $FeCl_2$, $SbCl_5$, $AlCl_3$ and other metal halides. Because they suppress equilibration reactions due to siloxane bond rearrangement, selectively bring about the ring-opening reaction of the target hexamethylcyclotrisiloxane, and can suppress undesirable side reactions, metal halides exhibiting Lewis acid properties are preferable, with $ZnCl_2$ being especially preferable. Also, the activity of the catalyst in the ring-opening reaction can be conspicuously increased by using acid halides or acid anhydrides together with the metal halides exhibiting Lewis acid properties. Catalysts composed of such metal halides exhibiting Lewis acid properties and acid halides or acid anhydrides are known as Friedel-Crafts acylation reaction catalysts. Such catalysts consist of a metal halide exhibiting Lewis acid properties and an acid halide or an acid anhydride. Although the mole ratio is arbitrary, 1 moL of acid halide and 0.5 moL of acid anhydride per 1 moL of metal halide is preferable stoichiometrically. In practice, however, it is preferable to use them in equivalent or greater amounts. Also, it is preferable that the acyl groups in the acid halides or acid anhydrides used in the catalysts should be the same as the acyl group represented by the general formula:

$$\begin{array}{c} -C-R^2 \\ \| \\ O \end{array}$$

in the acyloxysilane represented by the general formula indicated above.

Next, 1-hydroxy-organotetrasiloxane represented by the general formula (II) or an organosiloxane oligomer mixture comprising it as the main component is prepared by hydrolyzing 1-acyloxy-organotetrasiloxane represented by the general formula (I) or an organosiloxane oligomer mixture comprising it as the main component. When 1-acyloxy-organotetrasiloxane represented by the general formula (I) is hydrolyzed, the reaction must be conducted carefully so as to suppress siloxane bond rearrangement and dimerization of the 1-hydroxy-organosiloxane represented by the general formula (II), which is produced by hydrolysis. The hydrolysis can be conducted under milder conditions than in the case of hydrolyzing conventional 1-halo-organotetrasiloxanes. When the 1-acyloxy-organotetrasiloxane represented by the general formula (I) is hydrolyzed, it is preferable to hydrolyze 1-acyloxy-organotetrasiloxane represented by the general formula (I) in the presence of an alkali metal or alkaline earth metal carbonate. Alkali metal carbonates are exemplified by sodium hydrogencarbonate, sodium carbonate, potassium carbonate, lithium carbonate, and the like, and alkaline earth metal carbonates are exemplified by magnesium carbonate, calcium carbonate, barium carbonate, and the like. The amount of addition of these alkali metal or alkaline earth metal carbonates is, preferably, between 0.5 and 1.5 moL per 1 moL of 1-acyloxy-organotetrasiloxane represented by the general formula (I). Also, in order to promote hydrolysis, it is preferable to add triethylamine, pyridine, piperidine, quinoline, diethylhydroxyamine, and other amine compounds. The amount of addition of these amine compounds is, preferably, between 0.0001 and 1 moL per 1 moL of 1-acyloxy-organotetrasiloxane represented by the general formula (I). Also, although the hydrolysis proceeds even in the absence of an organic solvent, it can be conducted in the presence of an organic solvent, such as toluene, xylene, and other aromatic hydrocarbons; diethyl ether, tetrahydrofuran, and other ethers; chloroform, carbon tetrachloride, methylene chloride, and other chlorinated hydrocarbons. Also, a temperature of −10° C. to 100° C. is preferable, and a temperature of 0° C. to 50° C. is especially preferable as the reaction temperature used for the hydrolysis.

Next, organopentasiloxane represented by the general formula (IV) or an organosiloxane oligomer mixture comprising it as the main component is obtained by subjecting (A) 1-hydroxy-organotetrasiloxane, or an organosiloxane oligomer mixture comprising it as the main component, which is obtained by hydrolyzing 1-acyloxy-organotetrasiloxane or an organosiloxane oligomer mixture comprising it as the main component, and (B) hydrolytic silane represented by the general formula (III) to a condensation reaction. The organosiloxane oligomer mixture comprising organopentasiloxane represented by the general formula (IV) as the main component means a mixture of organosiloxane oligomers, in which a hydrolytic group is bonded to a silicon atom at the end of the molecular chain as represented by the general formula (IV), but the number of siloxane units varies. X in the general formula (III) is a hydrolytic group bonded to a silicon atom, and is specifically exemplified by methoxy, ethoxy, propoxy, butoxy, pentyloxy, hexyloxy and other alkoxy groups; vinyloxy, allyloxy, butenyloxy, hexenyloxy, isopropenyloxy, and other alkenyloxy groups; phenyloxy, tolyloxy, xylyloxy, and other aryloxy groups; benzyloxy, phenetyloxy, and other arylalkoxy groups; acetoxy, propionyloxy, benzoyloxy, and other acyloxy groups; chlorine atoms, bromine atoms, iodine, and other halogen atoms, and, preferably, alkoxy or acyloxy groups. Also, the subscript n in the general formula (III) is 0, 1, or 2. Preferably, the subscript n is 0. When the subscript n is 0, the organopentasiloxane represented by the general formula (IV) obtained by the condensation reaction is trifunctional, when the subscript n is 1, it is difunctional, and when the subscript n is 2, it is monofunctional.

The condensation reaction is promoted by mixing and heating 1-hydroxy-organotetrasiloxane represented by the general formula (II) or an organosiloxane oligomer mixture comprising it as the main component and a hydrolytic silane represented by the general formula (III). Also, condensation reaction catalysts can be added in order to promote the condensation reaction. Such condensation reaction catalysts are exemplified by acetic acid, propionic acid, acrylic acid, and other carboxylic acids; carbonic acid, hydrochloric acid, sulfuric acid, and other inorganic acids; sodium oxide, potassium hydroxide, lithium hydroxide, calcium hydroxide, magnesium hydroxide, and other inorganic bases; triethylamine, pyridine, piperidine, quinoline, diethylhydroxylamine, and other amines. Also, there are no particular limitations concerning the amount of addition of the hydrolytic silane represented by the general formula (III) relative to the 1-hydroxy-organotetrasiloxane represented by the general formula (II) as long as there is an excessive molar amount of the hydrolytic silane. The temperature of the condensation reaction is, preferably, between 70° C. and 130° C. This is due to the fact that when the reaction temperature is less than 70° C., the condensation reaction does not proceed quickly, and when the temperature exceeds 130° C., the siloxane bonds of the obtained organopentasiloxane become prone to rearrangement. As the occasion demands, the organopentasiloxane represented by the general formula (IV) can be efficiently prepared by fractional distillation of the organopentasiloxane represented by the general formula (IV), or an organosiloxane oligomer mixture comprising it as the main component, which is obtained by the condensation reaction of the hydrolytic silane represented by the general formula (III) and 1-hydroxy-organotetrasiloxane represented by the general formula (II), or an organosiloxane oligomer mixture comprising it as the main component. When such fractional distillation is conducted, it is preferable to use oxygen, quinone compounds, amine compounds, hindered phenol compounds, phenothiazine, hindered phenols having an onium salt structure, and other polymerization inhibitors in order to prevent the reaction mixture from gelling.

Because the organopentasiloxane represented by the general formula (IV) obtained in this manner has an acryloyloxy-containing monovalent organic group or a methacryloyloxy-containing monovalent organic group bonded to a silicon atom at one end of the molecular chain and a hydrolytic group bonded to a silicon atom at the other end of the molecular chain, it can be used as a coupling agent and as raw material for the production of crosslinkable polyolefinic resins, and reinforcing inorganic fillers surface-treated therewith can be imparted with a fatigue durability that is superior to that of silicone rubbers.

EXAMPLES

The process for the production of organopentasiloxane of the present invention will be now explained by using application examples.

Example 1

25.8 g (314.3 mmoL) sodium acetate and 30 g toluene were placed in a four-neck flask furnished with an agitator and the system was subjected to azeotropic dehydration by heating it for 30 minutes at the reflux temperature of toluene. After that, the system was cooled to 75° C. and 63 g (285.7 mmoL) 3-methacryloyloxypropyl dimethylchlorosilane was added dropwise. When the dropwise addition was over, the system was heated for 30 minutes at 80° C. under agitation. When a portion of the reaction mixture was analyzed using gas chromatography ("GLC" below), the peak of 3-methacryloyloxypropyl dimethylchlorosilane had disappeared. After that, a toluene solution was obtained by filtering off the by-produced sodium chloride and unreacted sodium acetate. After removing toluene from a portion of this toluene solution, analysis using GLC, infrared spectroscopic analysis ("IR" below), ¹H-nuclear magnetic resonance analysis ("¹H—NMR" below) and gas chromatography-mass spectrometry ("GC—MS" below) showed that 3-methacryloyloxypropyl dimethylacetyloxysilane represented by the formula:

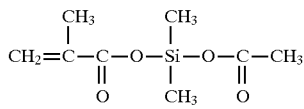

had been produced.

Next, when 7.6 g (56.5 mmoL) acetic anhydride and 3.5 g (25.7 mmoL) zinc chloride were placed in a separate four-neck flask furnished with an agitator and subjected to heating under agitation for 10 minutes at 70° C., zinc chloride was completely dissolved and a dark red solution was obtained. After cooling the solution to room temperature, the entire amount of the previously prepared toluene solution of 3-methacryloyloxypropyl dimethylacetyloxysilane, 63.4 g (285.7 mmoL) hexamethylcyclotrisiloxane, and 0.003 g 2,6-di-i-butyl-4-methylphenol were placed in the flask, and the system was heated at 50° C. for 3 hours 45 minutes under agitation. When a portion of the reaction mixture was analyzed using GLC, it was found that 3-methacryloyloxypropyl dimethylacetyloxysilane had been converted to 1-acetyloxy-7-(3-methacryloyloxypropyl)-1,1,3,3,5,5,7,7-octamethyltetrasiloxane represented by the formula:

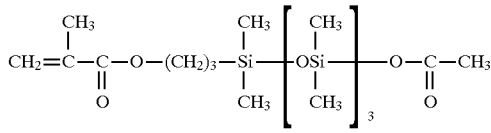

The ratio (reaction ratio) was 88%. After that, the system was neutralized by adding 2.9 g (28.3 mmoL) triethylamine. A toluene solution was obtained by removing the by-produced salt by decantation. 119.3 g of a liquid was obtained from this toluene solution by heating the low boiling point fraction at 90° C. for 1 hour under a reduced pressure of 1 mmHg. Analysis of a portion of this liquid using ¹H—NMR, IR, and GC—MS showed that it consisted of an organosiloxane oligomer mixture comprising 1-acetyloxy-7-(3-methacryloyloxypropyl)-1,1,3,3,5,5,7,7-octamethyltetrasiloxane as the main component, with the content of the siloxane determined by GLC being 65%.

Subsequently, after adding the entire amount of the liquid, 30 g toluene, 100 g water, 26.4 g (314.3 µmoL) sodium hydrogencarbonate and 1.59 g triethylamine (15.7 µmoL), the system was subjected to agitation for 2.5 hours at room temperature. When a portion of the reaction mixture was analyzed by using GLC, the peak of 1-acetyloxy-1-acetyloxy-7-(3-methacryloyloxypropyl)-1,1,3,3,5,5,7,7-octamethyltetrasiloxane had disappeared. After that, a toluene solution obtained by removing water from the system was washed twice. A liquid was obtained after removing toluene by heating the toluene solution in an evaporator under reduced pressure. Analysis of a portion of this liquid using GLC, IR, ¹H—NMR, and GC—MS showed that it consisted of an organosiloxane oligomer mixture comprising 1-acetyloxy-1-acetyloxy-7-(3-methacryloyloxypropyl)-1,1,3,3,5,5,7,7-octamethyltetrasiloxane represented by:

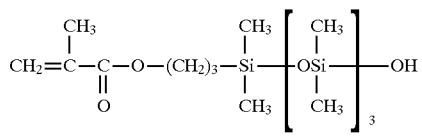

as the main component, the content of the siloxane determined by GLC being 50%.

Upon adding 47.8 g (314.3 µmoL) tetramethoxysilane and 0.15 g calcium hydroxide to the entire amount of the liquid, the system was subjected to heating under agitation for 10 minutes at the reflux temperature of tetramethoxysilane. After that, upon filtering off calcium hydroxide from the system and adding 0.12 g 3,5-di-t-butyl-4-hydroxyphenylmethyldimethylammonium chloride, 0.012 g hydroquinone monomethyl ether, and 0.012 g 2,6-di-t-butyl-4-methylphenol, 51.4 g (corresponds to a yield of 33%) of the 140°–153° C./1 mmHg fraction was obtained by heating under reduced pressure. Analysis of the fraction using GLC, IR, and NMR showed that it consisted of an organosiloxane oligomer mixture, 85.3% of which was constituted by 1,1,1-trimethoxy-9-(3-methacryloyloxypropyl)-3,3,5,5,7,7,9,9-octamethylpentasiloxane represented by the formula:

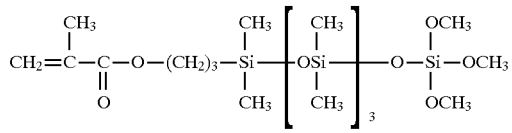

Also, it was also found that this mixture did not contain 1,1,1-trimethoxy-9-methacryloxy-3,3,5,5,7,7,9,9-octamethylpentasiloxane represented by the formula:

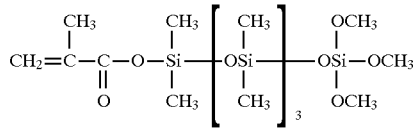

and 1,1,1-trimethoxy-9-propyl-3,3,5,5,7,7,9,9-octamethylpentasiloxane represented by the formula:

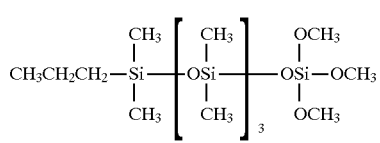

Comparison Example 1

16.6 g (131.4 µmoL) allyl methacrylate, 25 µL hexane, and 0.01 g 2,6-di-t-butyl-4-methylphenol were placed in a four-neck flask furnished with an agitator and subjected to azeotropic dehydration for 30 minutes. Next, after adding 1,1,3,3-tetramethyl-1,3-divinyldisiloxane complex of platinum to the system in such a manner that the amount of platinum metal relative to allyl methacrylate was 20 ppm, 50 g (119.4 µmoL) of 1,1,1-trimethoxy-3,3,5,5,7,7,9,9-octamethylpentasiloxane represented by the formula:

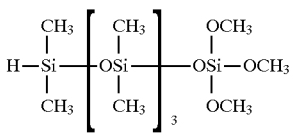

was added dropwise at 70° C. When the dropwise addition was over, hexane was removed by elution from a portion of the reaction mixture, whereupon analysis using GLC, $^1$H—NMR, IR, and GC—MS showed that it consisted of an organopolysiloxane mixture, 62% of which was constituted by 1,1,1-trimethoxy-9-(3-methacryloyloxypropyl)-3,3,5,5,7,7,9-octamethylpentasiloxane represented by the formula:

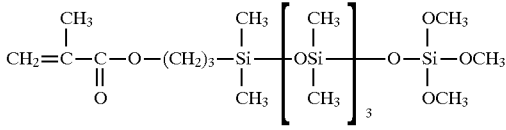

and it was found that the mixture contained 34% 1,1,1-trimethoxy-9-methacryloyloxy-3,3,5,5,7,7,9,9-octamethylpentasiloxane represented by the formula:

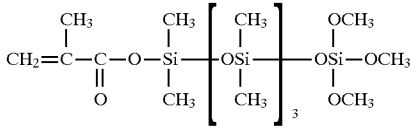

3% 1,1,1-trimethoxy-9-propyl-3,3,5,5,7,7,9,9-octamethylpentasiloxane represented by the formula:

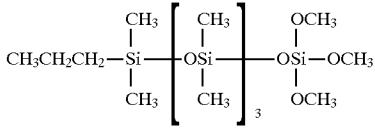

and 1% of other organosiloxane oligomers.

Thus it has been shown that the process for the production of organopentasiloxane of the present invention is characterized by permitting efficient production of organopentasiloxane having an acryloyloxy-containing monovalent organic group or a methacryloyloxy-containing monovalent organic group bonded to a silicon atom at one end of the molecular chain and a hydrolytic group bonded to a silicon atom at the other end of the molecular chain.

What I claim is:

1. A process for the production of an organopentasiloxane, comprising the step of (A) condensing a 1-hydroxy-organotetrasiloxane with a hydrolytic silane, wherein:

the 1-hydroxy-organotetrasiloxane has the general formula:

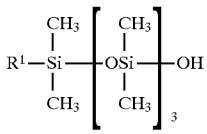

wherein R$^1$ is an acryloyloxy-containing monovalent organic group or a methacryloyloxy-containing monovalent organic group, and the hydrolytic silane has the general formula:

wherein R$^3$ is a monovalent hydrocarbon group, X is a hydrolytic group, and the subscript n is 0, 1, or 2.

2. The process according to claim 1, wherein the 1-hydroxy-organotetrasiloxane comprises not less than 30% of an organosiloxane oligomer mixture.

3. The process according to claim 1, wherein R$^1$ is an acryloyloxyalkyl group or a methacryloyloxyalkyl group.

4. The process according to claim 3, wherein the methacryloyloxyalkyl group is 3-methacryloyloxypropyl.

5. The process according to claim 1, wherein the 1-hydroxy-organotetrasiloxane is prepared by hydrolyzing a 1-acyloxy-organotetrasiloxane having the formula:

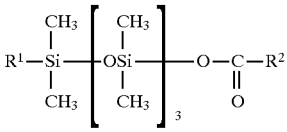

wherein R$^1$ is defined as above and R$^2$ is a monovalent hydrocarbon group.

6. The process according to claim 5, wherein the 1-acyloxy-organotetrasiloxane comprises than 50% of an organosiloxane oligomer mixture.

7. The process according to claim 5, wherein the 1-acyloxy-organotetrasiloxane is prepared by reacting hexamethylcyclotrisiloxane with an acyloxysilane in the presence of an acidic catalyst, wherein the acyloxysilane has the general formula:

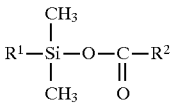

wherein R$^1$ and R$^2$ are as defined above.

8. The process according to claim 7, wherein the acidic catalyst is selected from the group consisting of a protonic acid catalyst and a metal halide exhibiting Lewis acid properties.

9. The process according to claim 8, wherein the protonic acid catalyst is trifluoromethanesulfonic acid.

10. The process according to claim 8, wherein the metal halide is zinc chloride.

11. The process according to claim 7, wherein the acidic catalyst is a Friedel-Crafts acylation reaction catalyst consisting of a metal halide exhibiting Lewis acid properties and an acid halide.

12. The process according to claim 11, wherein the mole ratio of acid halide to metal halide is at least 1:1.

13. The process according to claim 11, wherein the acid halide contains an acyl group having the general formula:

wherein R$^2$ is the same monovalent hydrocarbon group present in the acyloxysilane.

14. The process according to claim 7, wherein the acidic catalyst is a Friedel-Crafts acylation reaction catalyst consisting of a metal halide exhibiting Lewis acid properties and an acid anhydride.

15. The process according to claim 14, wherein the mole ratio of acid anhydride to metal halide is 0.5:1.

16. The process according to claim 14, wherein the mole ratio of acid anhydride to metal halide is at least 1:1.

17. The process according to claim 14, wherein the acid anhydride contains an acyl group having the general formula:

$$-\underset{\underset{O}{\|}}{C}-R^2$$

wherein $R^2$ is the same monovalent hydrocarbon group present in the acyloxysilane.

18. The process according to claim 5, wherein the 1-acyloxy-organotetrasiloxane is hydrolyzed in the presence of a metal carbonate selected from the group consisting of an alkali metal carbonate and an alkaline earth metal carbonate.

19. The process according to claim 18, wherein the metal carbonate is present in an amount ranging from 0.5 to 1.5 moles per one mole of the 1-acyloxy-organotetrasiloxane.

20. The process according to claim 18, wherein the 1-acyloxy-organotetrasiloxane is also hydrolyzed in the presence of an amine compound.

21. The process according to claim 20, wherein the amine compound is present in an amount ranging from 0.0001 to 1 mole per mole of the 1-acyloxy-organotetrasiloxane.

22. The process according to claim 5, wherein the 1-acyloxy-organotetrasiloxane is hydrolyzed in the presence of an organic solvent.

23. The process according to claim 5, wherein the 1-acyloxy-organotetrasiloxane is hydrolyzed at a temperature of from −10° to 100° C.

24. The process according to claim 23, wherein the 1-acyloxy-organotetrasiloxane is hydrolyzed at a temperature of from 0° to 50° C.

25. The process according to claim 1, wherein X is alkoxy or acyloxy and n is 0.

26. The process according to claim 1, wherein the 1-hydroxy-organotetrasiloxane and the hydrolytic silane are condensed in the presence of a condensation reaction catalyst.

27. The process according to claim 1, wherein the hydrolytic silane is present in a molar excess relative to the 1-hydroxy-organotetrasiloxane.

28. The process according to claim 1, wherein the 1-hydroxy-organotetrasiloxane and the hydrolytic silane are condensed at a temperature of from 70° to 130° C.

29. The process according to claim 1, further comprising the step of (B) fractionally distilling the organopentasiloxane in the presence of a polymerization inhibitor.

30. The product prepared according to the process of claim 1.

* * * * *